United States Patent [19]
Nishimura et al.

[11] Patent Number: 5,456,845
[45] Date of Patent: Oct. 10, 1995

[54] METHOD FOR SEPARATING A BLOOD MATERIAL INTO BLOOD COMPONENT PRODUCTS

[75] Inventors: Takao Nishimura; Kenji Kobayashi; Junko Sato, all of Oita, Japan

[73] Assignee: Asahi Medical Co., Ltd., Tokyo, Japan

[21] Appl. No.: 199,511

[22] Filed: Feb. 22, 1994

[30] Foreign Application Priority Data

Feb. 22, 1993 [JP] Japan ................................. 5-054688

[51] Int. Cl.⁶ .................... B01D 21/26; B01D 35/02
[52] U.S. Cl. ............... 210/782; 210/257.1; 210/435; 210/645; 210/767; 210/787; 604/406; 604/408; 604/410; 494/36; 494/37
[58] Field of Search ................... 210/232, 257.1, 210/206, 435, 477, 483, 484, 767, 782, 787, 645; 604/408, 409, 406, 410; 436/177; 494/36, 37, 45

[56] References Cited

U.S. PATENT DOCUMENTS

| | | | |
|---|---|---|---|
| 4,596,657 | 6/1986 | Wisdom | 210/206 |
| 4,753,739 | 6/1988 | Noble | 210/787 |
| 4,985,153 | 1/1991 | Kuroda et al. | 210/782 |
| 5,089,146 | 2/1992 | Carmen et al. | 210/782 |
| 5,092,996 | 3/1992 | Spielberg | 210/257.1 |
| 5,100,564 | 3/1992 | Pall et al. | 210/782 |
| 5,217,627 | 6/1993 | Pall et al. | 210/767 |

FOREIGN PATENT DOCUMENTS

| | | |
|---|---|---|
| 0591980 | 4/1994 | European Pat. Off. . |
| 2058578 | 5/1971 | France . |
| 9114010 | 1/1992 | Germany . |
| 4022700 | 1/1992 | Germany . |
| 1-249063 | 10/1989 | Japan . |
| 3-502094 | 5/1991 | Japan . |
| WO9104088 | 4/1991 | WIPO . |
| WO9220428 | 11/1992 | WIPO . |
| WO9220427 | 11/1992 | WIPO . |

*Primary Examiner*—John Kim
*Attorney, Agent, or Firm*—Birch, Stewart, Kolasch & Birch

[57] ABSTRACT

Disclosed is a method for separating a blood material into leukocyte-removed blood component products, which comprises providing a multiple blood bag system comprising a primary bag containing a blood material, a leukocyte-removing filter device comprising a flat casing, and at least one satellite bag, and centrifuging the blood material using a centrifuge cup having the multiple blood bag system accommodated therein, to thereby separate the blood material into blood components, wherein the centrifugation is performed with the filter device being held by a filter device holder having a substantially flat dimension which is disposed in a centrifuge cup so as to extend in a direction perpendicular to an inner bottom floor of the centrifuge cup, and wherein the filter device holder has a recess and the filter device is received by the recess in a manner such that a flat surface of the flat casing of the filter device is perpendicular to the inner bottom floor of the centrifuge cup. By the method of the present invention, not only can the accommodation of a multiple blood bag system into a centrifuge cup be readily performed without any additional cumbersome operations, but also the danger of damaging the filter device and the blood bags is extremely reduced or eliminated.

5 Claims, 9 Drawing Sheets

FIG.3(a)
FIG.3(b)
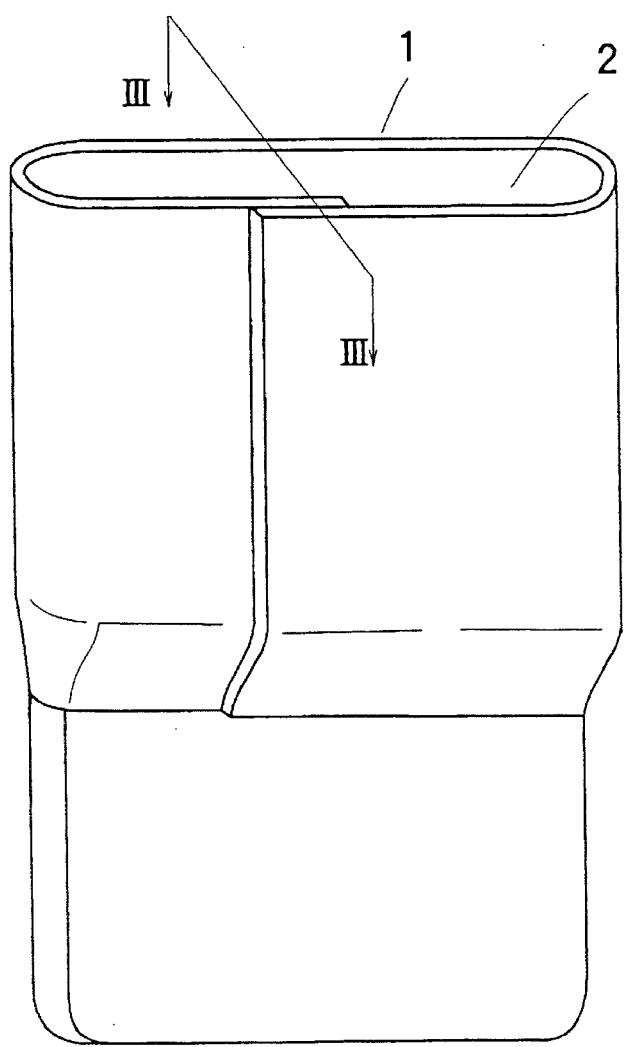
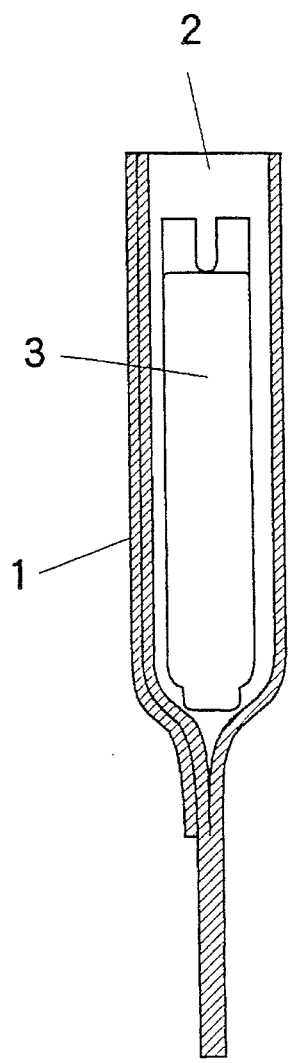

FIG.9(a)
FIG.9(b)
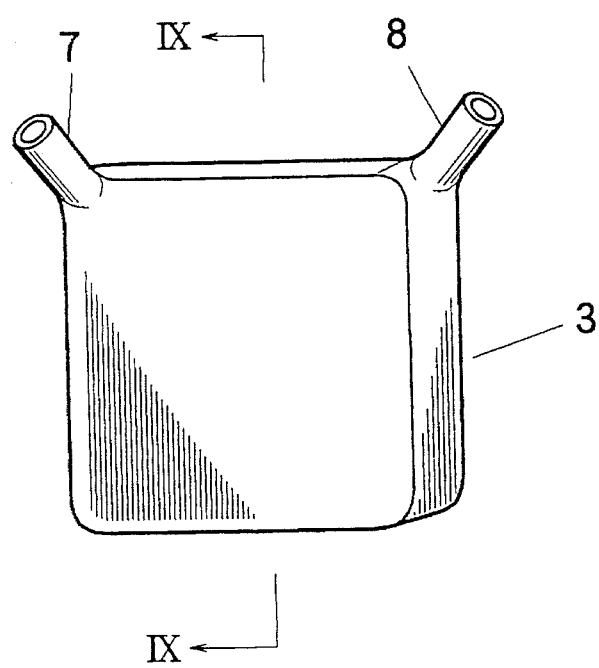
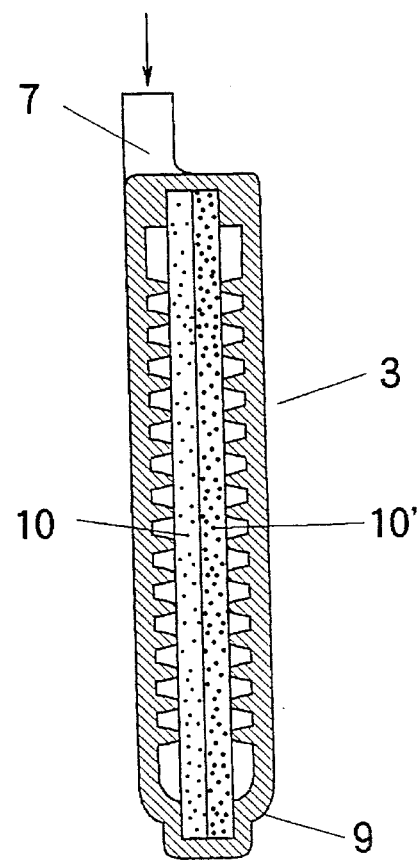

METHOD FOR SEPARATING A BLOOD MATERIAL INTO BLOOD COMPONENT PRODUCTS

BACKGROUND OF THE INVENTION

1. Field of The Invention

The present invention relates to a method for separating a blood material into blood component products. More particularly, the present invention is concerned with a method for separating a blood material into leukocyte-removed blood component products, which comprises providing a multiple blood bag system comprising a primary bag containing a blood material, a leukocyte-removing filter device comprising a flat casing, and at least one satellite bag, and centrifuging the blood material or a leukocyte-removed blood product obtained from the blood material, using a centrifuge cup having the multiple blood bag system accommodated therein, to thereby separate the blood material or leukocyte-removed blood product into blood components, wherein the centrifugation is performed with the filter device being held by a filter device holder having a substantially flat dimension, which extends in a direction perpendicular to an inner bottom floor of the centrifuge cup and is retained between blood bags of the multiple blood bag system or between a blood bag of the multiple blood bag system and an inner side wall of the centrifuge cup, and wherein the filter device holder has a recess and the filter device is received by the recess in a manner such that a flat surface of the flat casing of the filter device is perpendicular to the inner bottom floor of the centrifuge cup. By the method of the present invention, the filter device of the multiple blood bag system can be accommodated readily, fittedly and stably into a centrifuge cup together with the blood bags in a compact fashion without the need for using an adhesive tape, so that the accommodation of a multiple blood bag system into a centrifuge cup can be readily performed without any additional cumbersome operations. Further, since during the centrifugation, the flat filter device is stably retained in the centrifuge cup in a state received by the recess of the filter device holder extending in a direction perpendicular to the inner bottom floor of the centrifuge cup, the danger of damaging the filter device and the blood bags is extremely reduced or eliminated.

2. Discussion of Related Art

In recent years, in accordance with the progress of immunology and study of transfusion, it has become apparent that side effects of transfusion are caused by the leukocytes contained in a blood material used for transfusion. Side effects of transfusion include not only relatively mild side effects, such as headache, nausea, chilliness and non-hemolytic febrile transfusion reactions, but also serious side effects. With respect to the latter, particularly when a transfusion recipient has an immunopathy, transfusion is likely to cause serious side effects, such as graft versus host (GVH) reaction, in which transfused leukocytes attack the skin and internal organs of the recipient, infections by viruses present in the leukocytes, e.g., cytomegalovirus infection, and allosensitization. For effective prevention of such side effects of transfusion, it is now widely practiced to remove leukocytes from a blood material by means of a leukocyte-removing filter.

As filters for removing leukocytes from blood materials (such as whole blood, red cell concentrate, and platelet concentrate), various types of filters comprising a casing having an inlet for blood and an outlet for leukocyte-removed blood and, packed in the casing, a filter medium for removing leukocytes, have been put to practical use (see, for example, U.S. Pat. Nos. 4,701,267, 4,936,998, 4,880,548, 4,923,620, and 4,925,572).

Generally, it is difficult to connect a leukocyte-removing filter to a blood bag containing a collected blood material under aseptic conditions unless a special apparatus, such as an apparatus for aseptic connection, is used. Therefore, when a filter is connected to a blood bag containing a blood material without using a special apparatus for aseptic connection, there is a danger that the blood material is contaminated with microorganisms. Because of such a danger, it is usually required that a blood material for use in transfusion which has been treated for removing leukocytes under unsatisfactory conditions with respect to asepsis be used within 24 hours from the leukocyte-removing treatment. On the other hand, it has recently been reported that when the removal of leukocytes from a blood material is practiced under aseptic conditions immediately after the collection of the blood material from a donor, not only can the storage life of the leukocyte-removed blood material be prolonged, but also the damage to the red cells and platelets can be reduced. Accordingly, various systems containing a leukocyte-removing filter have been proposed for aseptically removing leukocytes from blood immediately after the collection of the blood (see, for example, U.S. Pat. No. 4,596,657).

As a system containing a leukocyte-removing filter, which can be used for aseptically removing leukocytes from blood immediately after the collection of the blood, U.S. Pat. No. 4,596,657 discloses a multiple blood bag system comprising a primary bag (as a blood collection bag), and a plurality of satellite bags, one of which is connected to the primary bag (blood collection bag) through a leukocyte-removing filter. The use of such a leukocyte-removing multiple blood bag system involves an operation in which blood is collected in the primary bag and the primary bag containing the blood is placed in a centrifuge cup together with the filter and the satellite bags, and the blood is subjected to centrifugation so as to be separated into a plasma layer (containing or not containing platelets depending on the centrifugation conditions) and a red cell concentrate layer.

Recently, a multiple blood bag system of the above-mentioned U.S. Pat. No. 4,596,657 has been introduced to the market, which employs as the filter a disk-like leukocyte-removing filter (disclosed in, for example, Unexamined Japanese Patent Application Laid-Open Specification Nos. 3-502094 and 1-249063) having a configuration and a cross-section shown in FIGS. 7(a) and 7(b), respectively. This disk-like filter employs a casing composed of a disk-like main body having a blood inlet and a blood outlet which protrude outwardly of the planes of both sides of the main body. However, actual experiments conducted using this commercially available multiple blood bag system, have revealed that it is very difficult to fittedly and stably accommodate the filter in a centrifuge cup together with the primary bag and the satellite bags. For example, when the filter is placed above the blood bags in the centrifuge cup as instructed in the manual accompanying the multiple blood bag system, the filter is unstable in the centrifuge cup, so that there is a danger that the filter is likely to be out of the centrifuge cup during centrifugation. For preventing the filter from being out of the centrifuge cup, it is necessary to fix the filter to the centrifuge cup together with the blood bags by means of an adhesive tape after the filter has been placed above the blood bags, thereby securing the entire multiple blood bag system to the centrifuge cup. This operation is extremely cumbersome. Further, even this operation cannot prevent the occurrence of damage to the filter and the blood bags due to the centrifugal force. On the other hand, when the filter is placed directly on the bottom of the centrifuge and under the blood bags, or the filter is placed between blood bags arranged one upon another, or the filter is placed between blood bags arranged side by side, it is difficult to compactly, fittedly and stably accommodate the entire multiple blood bag system in the centrifuge, leading to a danger that the filter and the bags are very likely to be destroyed due to the centrifugal force and the friction between the bags and the filter during centrifugation.

In order to solve the above problems, U.S. Pat. No. 5,100,564 discloses the use of a support means which is provided so as to engage the upper circumference of the centrifuge cup and which supports the filter thereon under the centrifugal force. In U.S. Pat. No. 5,100,564, when the multiple blood bag system is to be placed in a centrifuge cup, the blood bags are first placed in the centrifuge cup and then the support means is placed so as to engage the upper circumference of the centrifuge cup, and subsequently the filter is set on the support means. However, not only is the use of this support means cumbersome, but also the support means inevitably largely separates the filter means from the blood bags, so that it is impossible to attain compact accommodation of the multiple blood bag system in the centrifugal cup. Further, with this support means, there is a danger that the filter is inadvertently released from the support means and is out of the centrifuge cup together with circuit tubes during centrifugation, so that it is necessary to fix the filter to the support means by means of an adhesive tape or the like. Because of these problems, this technique has not been widely used.

With respect to the multiple blood bag system of U.S. Pat. No. 4,596,657 mentioned above, it is conceivable to incorporate therein a flat square filter as the filter instead of the disk-like filter employed therein. However, actual experiments conducted using a multiple blood bag system of U.S. Pat. No. 4,596,657 in which a flat square filter having a configuration and a cross-section shown, respectively, in FIGS. 8(a) and 8(b) is employed have revealed that there occur substantially the same problems as in the case of the above-mentioned multiple blood bag system of U.S. Pat. No. 4,596,657 employing a disk-like filter shown in FIGS. 7(a) and 7(b). Illustratively stated, when the flat square filter is placed above the blood bags in the centrifuge cup, the filter is unstable in the centrifuge cup, so that there is a danger that the filter is likely to be out of the centrifuge cup during centrifugation. For preventing the filter from being out of the centrifuge cup, it is necessary to fix the filter to the centrifuge cup together with the blood bags by means of an adhesive tape after the filter has been placed above the blood bags, thereby securing the entire system to the centrifuge cup. On the other hand, when the filter is placed directly on the bottom of the centrifuge and under the blood bags, or the filter is placed between blood bags arranged one upon another, or the filter is placed between blood bags arranged side by side, it is difficult to compactly, fittedly and stably accommodate the entire multiple blood bag system in the centrifuge, leading to a danger that the filter and the bags are likely to be destroyed due to the centrifugal force and the friction between the bags and the filter during centrifugation.

With respect to the above-mentioned flat square filter incorporated in the multiple blood bag system of U.S. Pat. No. 4,596,657, it is conceivable to modify the structure of the casing of the flat square filter so that the inlet and the outlet are located at the upper corners as shown in FIG. 9(a). When a filter having a configuration and a cross-section shown, respectively, in FIGS. 9(a) and 9(b) is placed between blood bags arranged side by side, it becomes less likely that the filter and the bags are destroyed due to the centrifugal force and the friction between the bags and the filter during centrifugation. However, the danger of damaging the filter device and the blood bags during centrifugation still remains. Since a leukocyte-removing multiple blood bag system is medical equipment, it is desired for the method of treating a blood material by use of the multiple blood bag system to be free of the danger of damaging the multiple blood bag system in the centrifugation operation.

In addition, generally, when a multiple blood bag system is accommodated in a centrifuge cup, the position of the filter in the centrifuge cup has conventionally been rather arbitrarily selected, and the danger of damaging the filter and the blood bags due to the centrifugal force is increased depending on the selected position of the filter. Therefore, it is desired to ensure that the filter is fittedly and stably accommodated at the most appropriate position in the centrifuge cup.

SUMMARY OF THE INVENTION

The present inventors have made extensive and intensive studies with a view toward developing a novel method for separating a blood material into leukocyte-removed blood component products using a multiple blood bag system, which is free from the above-mentioned problems inevitably accompanying the conventional methods. As a result, it has unexpectedly been found that the above-mentioned problems can be solved by a novel method for separating a blood material into leukocyte-removed blood component products, wherein the centrifugation is performed with the filter device being held by a filter device holder having a substantially flat dimension, which extends in a direction perpendicular to an inner bottom floor of the centrifuge cup and is retained between blood bags of the multiple blood bag system or between a blood bag of the multiple blood bag system and an inner side wall of the centrifuge cup, and wherein the filter device holder has a recess and the filter device is received by the recess in a manner such that a flat surface of the flat casing of the filter device is perpendicular to the inner bottom floor of the centrifuge cup. That is, by the above novel method of the present invention, the filter device of the multiple blood bag system can be accommodated readily, fittedly and stably into a centrifuge cup together with the blood bags in a compact fashion without the need for using an adhesive tape, so that the accommodation of a multiple blood bag system into a centrifuge cup can be readily performed without any additional cumbersome operations. Further, since during the centrifugation, the flat filter device is stably retained in the centrifuge cup in a state received by the recess of the filter device holder extending in a direction perpendicular to the inner bottom floor of the centrifuge cup, the danger of damaging the filter device and the blood bags is extremely reduced or eliminated.

Based on the above novel finding, the present invention has been completed.

Accordingly, it is a primary object of the present invention to provide a novel method for separating a blood material into leukocyte-removed blood component products using a multiple blood bag system, in which not only can the filter device of the multiple blood bag system be accommodated readily, fittedly and stably into a centrifuge cup together with the blood bags in a compact fashion without the need for using an adhesive tape or the like, so that the accommodation of a multiple blood bag system into a centrifuge cup can be readily performed without any additional cumbersome operations, but also the danger of damaging the filter device and the blood bags during centrifugation is effectively eliminated.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only and, thus, are not limitative of the present invention, and wherein:

FIG. 3(a) is a diagrammatic perspective view of another form of the filter device holder (encloser type) to be used in the method of the present invention;

FIG. 3(b) is a cross-sectional view of FIG. 3(a), taken along line III—III, shown with a filter device of the same type as in FIG. 2 which is indicated in side view;

FIGS. 9(a) is a diagrammatic perspective view of a further form of the filter device to be used in the method of the present invention; and FIG. 9(b) is an enlarged, cross-sectional view of FIG. 9(a), taken along line IX—IX.

In FIG. 1 through FIG. 9(b), like parts or portions are designated by like numerals.

DETAILED DESCRIPTION OF THE INVENTION

Figure 1:
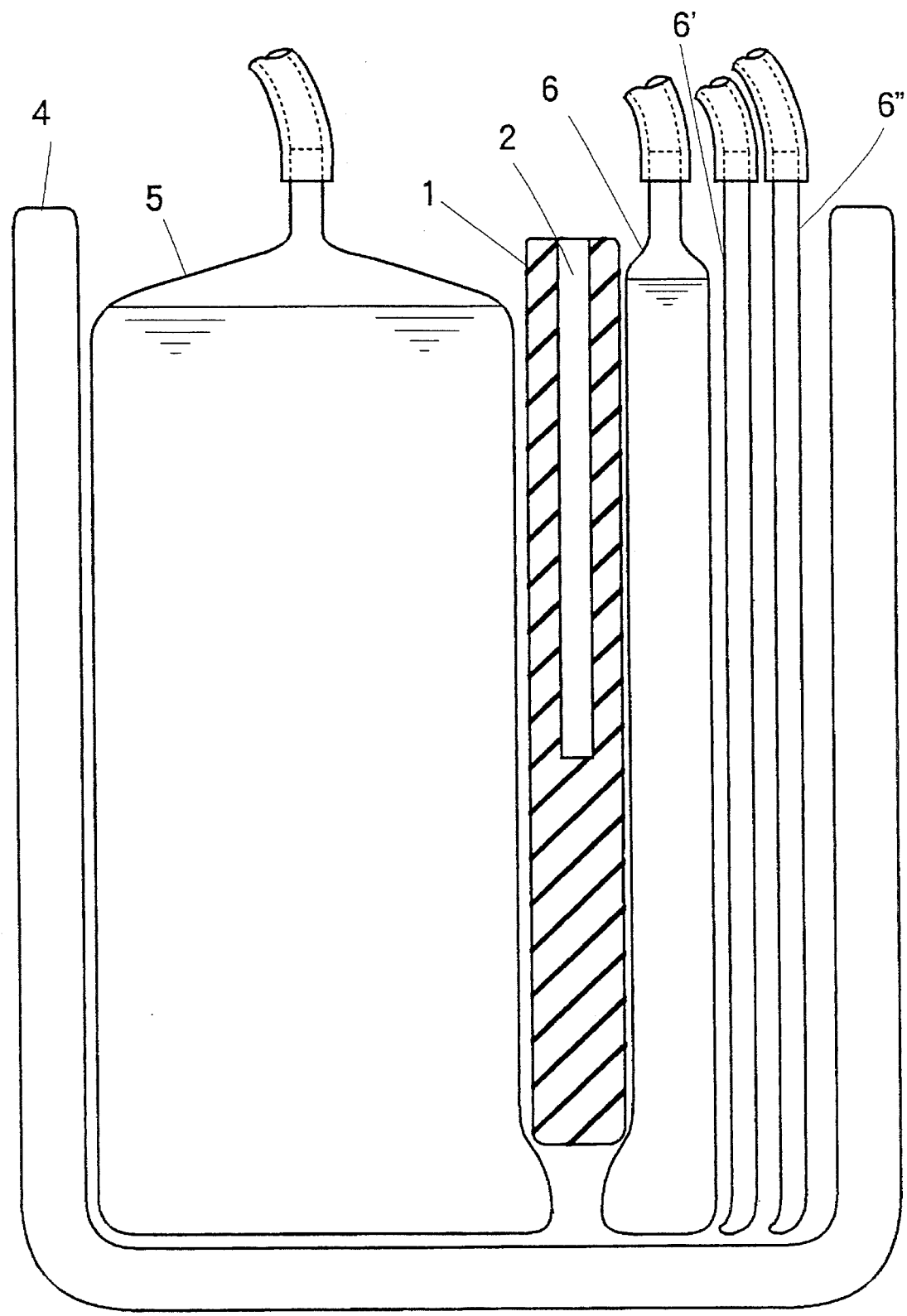
FIG. 1 is a diagrammatic view showing a manner in which a multiple blood bag system and a filter device holder shown in FIG. 2 holding the leukocyte-removing filter device (not shown), are stably accommodated in a centrifuge cup, with the filter device holder depicted in cross-section and with a front side of the centrifuge cup taken away to show the interior of the centrifuge cup.

According to the present invention, there is provided a method for separating a blood material into leukocyte-removed blood component products, which comprises:

(1) providing a multiple blood bag system comprising a primary bag containing a blood material, a leukocyte-removing filter device fluid-tightly connected to an outlet of the primary bag through a tube and at least one satellite bag fluid-tightly connected to an outlet of the filter device through a tube, the filter device comprising a flat casing having a blood inlet and a blood outlet, and a filter material disposed in the casing and communicated on one side thereof to the blood inlet and on the other side thereof to the blood outlet, and (2) in either order,
(a) centrifuging the blood material or a leukocyte-removed blood product obtained in step (b) from the blood material, using a centrifuge cup having the multiple blood bag system accommodated therein, to separate the blood material or leukocyte-removed blood product into blood components, and (b) filtering leukocytes from the blood material or a blood component separated in step (a) from the blood material, using the filter device of the multiple blood bag system, to obtain a leukocyte-removed blood product, wherein in step (a), the centrifugation is performed with the filter device of the multiple blood bag system being held by a filter device holder having a substantially flat dimension which is disposed in the centrifuge cup in a manner such that a plane of the filter device holder which extends along the substantially flat dimension is perpendicular to an inner bottom floor of the centrifuge cup and that the filter device holder is retained between blood bags of the multiple blood bag system or between a blood bag of the multiple blood bag system and an inner side wall of the centrifuge cup, the filter device holder having a recess substantially conforming to the shape of the flat casing of the filter device, the filter device being received by the recess of the filter device holder in a manner such that a flat surface of the flat casing of the filter device is perpendicular to the inner bottom floor of the centrifuge cup.

In the present invention, use is made of a multiple blood bag system comprising a primary bag, a leukocyte-removing filter device fluid-tightly connected to an outlet of the primary bag through a tube and at least one satellite bag fluid-tightly connected to an outlet of the filter device through a tube. As shown in FIGS. 7(a) through 9(b), filter device 3 of the multiple blood bag system comprises flat casing 9 having blood inlet 7 and blood outlet 8, and filter material 10 (or 10, 10') disposed in casing 9 and communicated on one side thereof to blood inlet 7 and on the other side thereof to blood outlet 8. In the present invention, various customary multiple blood bag systems can be employed. Examples of customary multiple blood bag systems employable in the present invention include those disclosed in U.S. Pat. Nos. 4,596,657, 4,767,541, 4,919,823, 4,810,378, 4,915,848, 5,092,996, 5,100,564, 5,089,146, 4,985,153, and 4,997,577, WO 92/20427, WO 92/20428, WO 91/04088, and German Patent Application 4022700 A1. With respect to the manner of connection among the filter device and the blood bags through tubes, reference can be made to these patent documents.

Figure 7A:
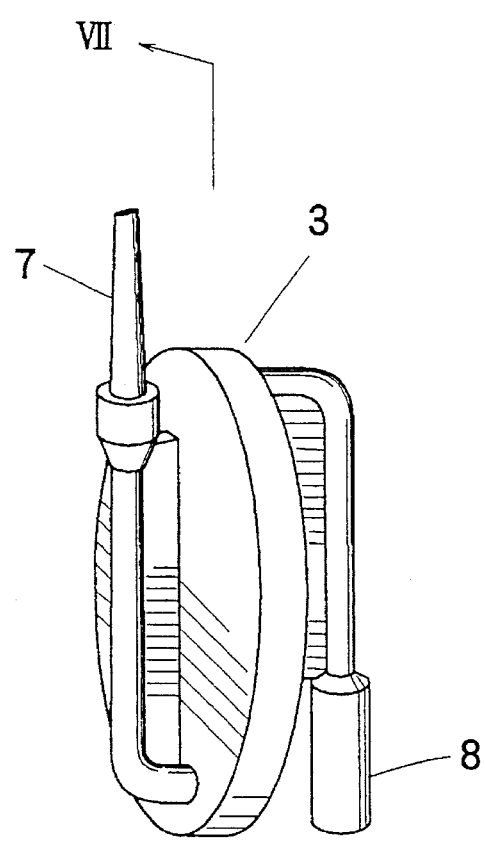
FIGS. 7(a) is a diagrammatic perspective view of one form of the filter device to be used in the method of the present invention.
Figure 7B:
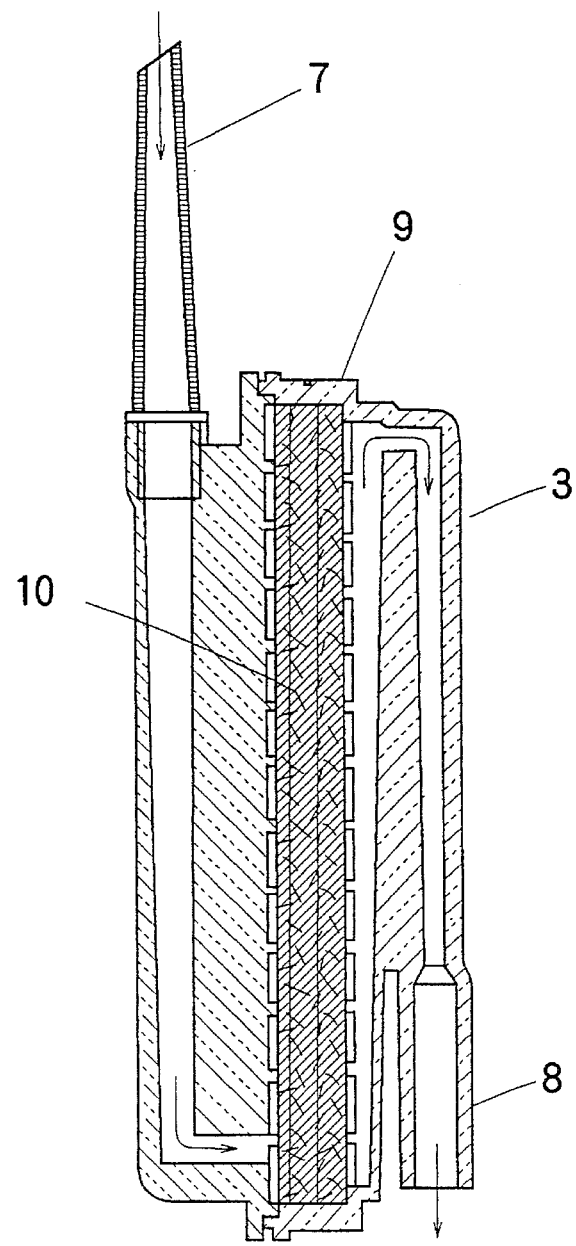
FIG. 7(b) is an enlarged, cross-sectional view of FIG. 7(a), taken along line VII—VII.
Figure 8A:
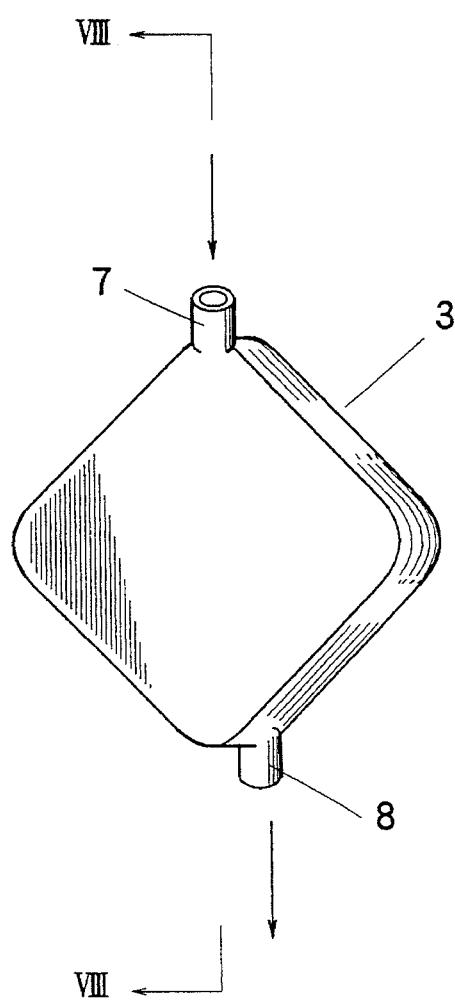
FIGS. 8(a) is a diagrammatic perspective view of another form of the filter device to be used in the method of the present invention.
Figure 8B:
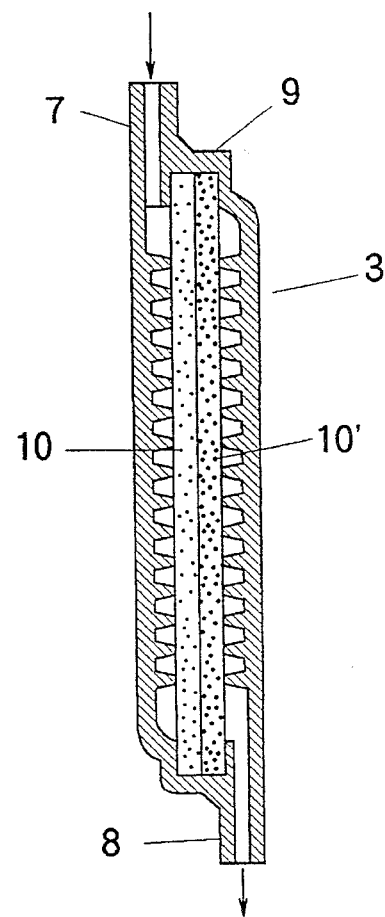
FIG. 8(b) is an enlarged, cross-sectional view of FIG. 8(a), taken along line VIII—VIII.

With respect to the configuration and structure of the filter device of the multiple blood bag to be used in the present invention, there is no particular limitation as long as it comprises a flat casing having a blood inlet and a blood outlet, and a filter material disposed in the casing and communicated on one side thereof to the blood inlet and on the other side thereof to the blood outlet. Examples of filter devices usable in the present invention include those shown in FIGS. 7(a) through 9(b). In FIG. 7(b), filter device 3 contains single filter material layer 10, and in FIGS. 8(b) and 9(b), filter device 3 contains a couple of filter material layers, 10, 10'.

In the present invention, it is preferred to use a filter device comprising a casing having a blood inlet and a blood outlet which are both located in a top portion of the casing. An example of such a filter device is shown in FIGS. 9(a) and 9(b). With respect to a filter device in which both the inlet and outlet are located on the top portion of the filter device, reference can be made to copending U.S. patent application Ser. No. 08/132,894 and European Patent Application No. 93 116 265.5.

The primary bag (blood collection bag) of the multiple blood bag system to be used in the method of the present invention contains a blood material, such as whole blood. The primary bag may also contain an anticoagulant mixed with the blood material.

The method of the present invention consists in the following steps (a) and (b), which can be performed in either order:

(a) centrifuging the blood material or a leukocyte-removed blood product obtained in step (b) from the blood material, using a centrifuge cup having the multiple blood bag system accommodated therein, to separate the blood material or leukocyte-removed blood product into blood components, and (b) filtering leukocytes from the blood material or a blood component separated in step (a) from the blood material, using the filter device of the multiple blood bag system, to obtain a leukocyte-removed blood product.

When step (a) is conducted prior to step (b), in step (a), the blood material, for example whole blood, is centrifuged using a centrifuge cup having the multiple blood bag system accommodated therein, to separate the blood material into blood components. By centrifugation, for example, whole blood is separated into an upper layer composed of plasma component and a lower layer composed of a red cell concentrate which contains leukocytes. (When the centrifugal force is relatively strong, the plasma obtained is platelet-poor plasma, whereas when the centrifugal force is relatively weak, the plasma obtained is platelet-rich plasma.) Then, in step (b), leukocytes are filtered from the blood component (red cell concentrate) separated in step (a) from the blood material, using the filter device of the multiple blood bag system, to obtain a leukocyte-removed blood product (red cell concentrate). On the other hand, when step (b) is conducted prior to step (a), in step (b), leukocytes are filtered from the blood material, for example whole blood, using the filter device of the multiple blood bag system, to obtain a leukocyte-removed blood product. Then, in step (a), the leukocyte-removed blood product obtained in step (b) from the blood material is centrifuged using a centrifuge cup having the multiple blood bag system accommodated therein, to separate the leukocyte-removed blood product into blood components, i.e., plasma component (as upper layer) and a red cell concentrate (as lower layer).

In step (a) of the method of the present invention, the centrifugation is performed with the filter device of the multiple blood bag system being held by a filter device holder having a substantially flat dimension which is disposed in the centrifuge cup in a manner such that a plane of the filter device holder which extends along the substantially flat dimension is perpendicular to an inner bottom floor of the centrifuge cup and that the filter device holder is retained between blood bags of the multiple blood bag system or between a blood bag of the multiple blood bag system and an inner side wall of the centrifuge cup.

The filter device holder to be used in the present invention has a recess substantially conforming to the shape of the flat casing of the filter device. In step (a), the filter device is received by the recess of the filter device holder in a manner such that a flat surface of the flat casing of the filter device is perpendicular to the inner bottom floor of the centrifuge cup.

In the present invention, the term "a filter device holder having a substantially flat dimension" means that the filter device holder has a thickness dimension which is small as compared to the length and width dimensions of the filter device holder.

In the method of the present invention, before step (a), the multiple blood bag system is accommodated in a centrifuge cup of a centrifuge. FIG. 1 is a diagrammatic view showing a manner in which a multiple blood bag system and filter device holder 1 shown in FIG. 2 holding the filter device (not shown) in recess 2, are stably accommodated in centrifuge cup 4. In FIG. 1, filter device holder 1 is depicted in cross-section and a front side of the centrifuge cup is taken away to show the interior of the centrifuge cup. In FIG. 1, filter device holder 1 is disposed between blood bags 5 and 6 of the multiple blood bag system having blood bags 5, 6, 6' and 6".

In the method of the present invention, it is desired that the centrifugal force to be applied to the filter device be as small as possible. Therefore, it is desired that the position of the filter device held by the filter device holder in the centrifuge cup be as high as possible, i.e., as close to the axis of rotation of the centrifuge as possible. Accordingly, it is preferred that the recess of the filter device holder be located in an upper portion thereof, so that the filter device is less influenced by a centrifugal force applied, as compared to a lower portion of the filter device holder.

With respect to the manner of retaining the filter device holder having the filter device held thereby in the centrifuge cup, when improved protection of the filter device is desired, it is preferred that the filter device holder having the filter device held thereby be disposed between blood bags of the multiple blood bag system placed in the centrifuge cup, so that the filter device is protected between blood bags, which have flexibility. On the other hand, for easier accommodation of the multiple blood bag system in the centrifuge cup, the filter device holder having the filter device held thereby may be disposed between a blood bag of the multiple blood bag system and an inner side wall of the centrifuge cup.

In the method of the present invention, the centrifugation may be conducted continuously or intermittently. When the centrifugation is intermittently conducted, the centrifugation may be intermitted once or more. During the intermission, the arrangement of the filter device holder having the filter device held thereby and the blood bags in the centrifuge cup may be changed, if desired.

The configuration or structure of the filter device holder to be used in the method of the present invention is not particularly limited as long as it has a substantially flat dimension and has a recess substantially conforming to the shape of the flat casing of the filter device, so that the recess being capable of receiving the filter device in a manner such that a flat surface of the flat casing of the filter device is perpendicular to the inner bottom floor of the centrifuge cup during centrifugation. For example, the filter device holder to be used in the method of the present invention may have any of the shapes shown in FIGS. 2 to 6. When the filter device has on the flat casing a projection, such as inlet and outlet nozzles, and/or an angular portion, it is preferred that the filter device holder have a portion thereof covering the projection and/or angular portion. With the above structure of the filter device holder, the filter device can be stably retained in the recess of the filter device holder during centrifugation.

There is no particular limitation with respect to the material for the filter device holder as long as the effects aimed at by the present invention are not impaired. However, from the viewpoint of improved protection of the filter device, it is preferred that the holder be made of an elastic material at least at a portion of the holder which contacts the filter device. An elastic material can effectively absorb any impact or stress which the holder having the filter device held thereby suffers during centrifugation, to thereby protect the filter device therefrom. Further, from the viewpoint of improved protection of the entire multiple blood bag system, it is more preferred that the entire filter device holder be made of an elastic material. Representative examples of elastic materials usable for producing the filter device holder include rubbers, plastics, fiber-reinforced plastics, silicone, and polymer blend resins.

Figure 2:
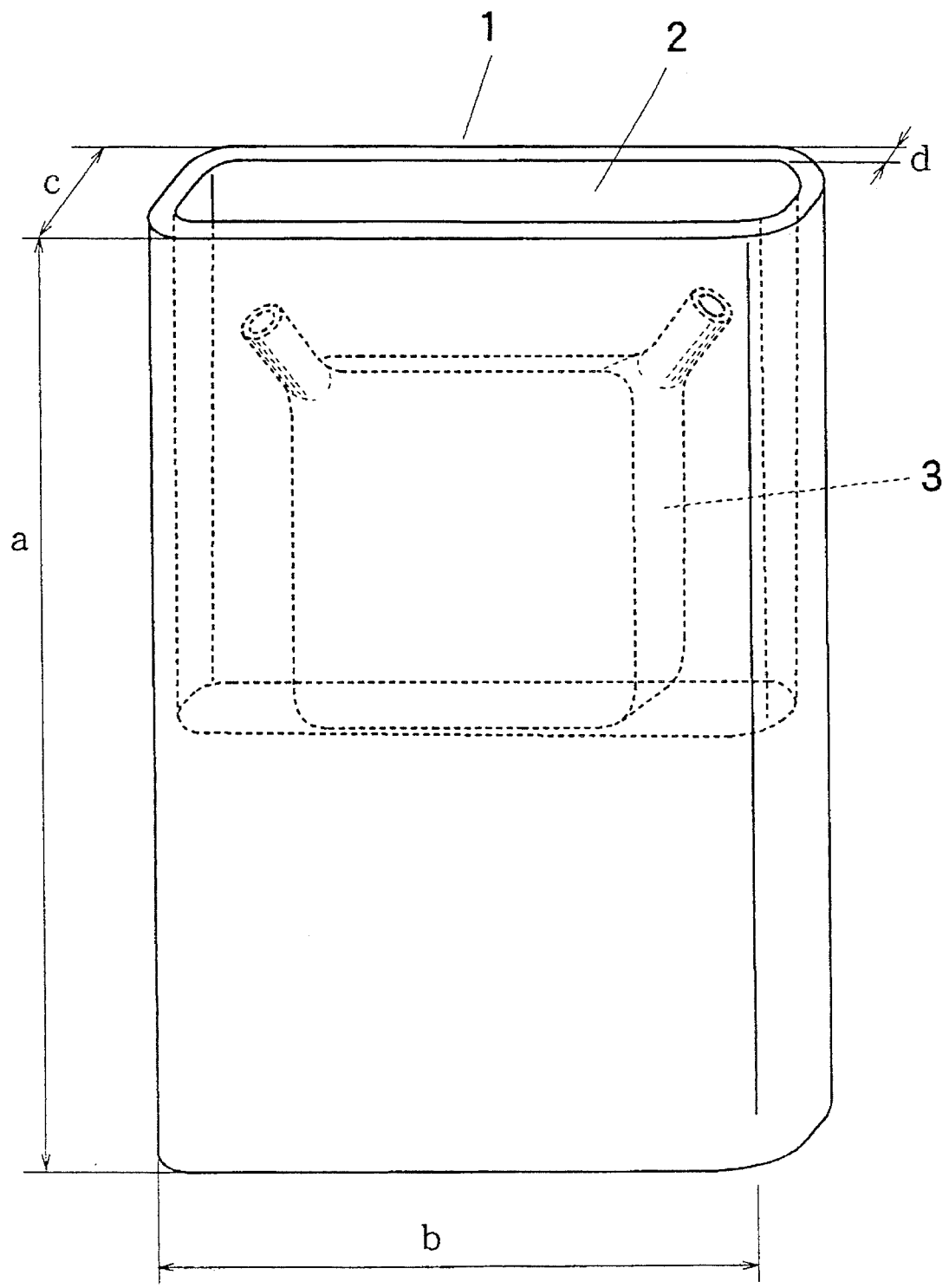
FIG. 2 is a diagrammatic perspective view of one form of the filter device holder (pocket type) to be used in the method of the present invention, shown with a filter device held thereby.

Referring now to FIGS. 2 through 6, the filter device holder to be used in the method of the present invention is described below in more detail. FIGS. 2. 3(*a*), 4, 5 and 6 are diagrammatic perspective views of various forms of the filter device holder to be used in the method of the present invention.

Filter device holder 1 of FIG. 2 is a pocket type holder holding filter device 3, and a pocket depicted with a broken line constitutes recess 2 for receiving filter device 3. In FIG. 2, the depth of recess 2 is larger than the height of filter device 3, so that all portions of the filter device which are likely to be exposed to stress during centrifugation are within the pocket of the filter device holder.

Filter device holder 1 of FIG. 3(*a*) is an encloser type holder having an enclosing wall which forms recess 2. The enclosing wall has both end portions which separably overlap, so that the enclosing wall is openable. The encloser type holder of FIG. 3(*a*) is advantageous in that due to the presence of the separably overlapping end portions in the enclosing wall, which render the enclosing wall openable and closable, accommodation of the filter device into and removal of the filter device from the recess of the filter device holder can be very readily performed. FIG. 3(*b*) is a cross-sectional side view of the filter device holder shown in FIG. 3(*a*), taken along line III—III of FIG. 3(*a*), shown with filter device 3 of the same type as in FIG. 2 which is indicated in side view.

Figure 4:
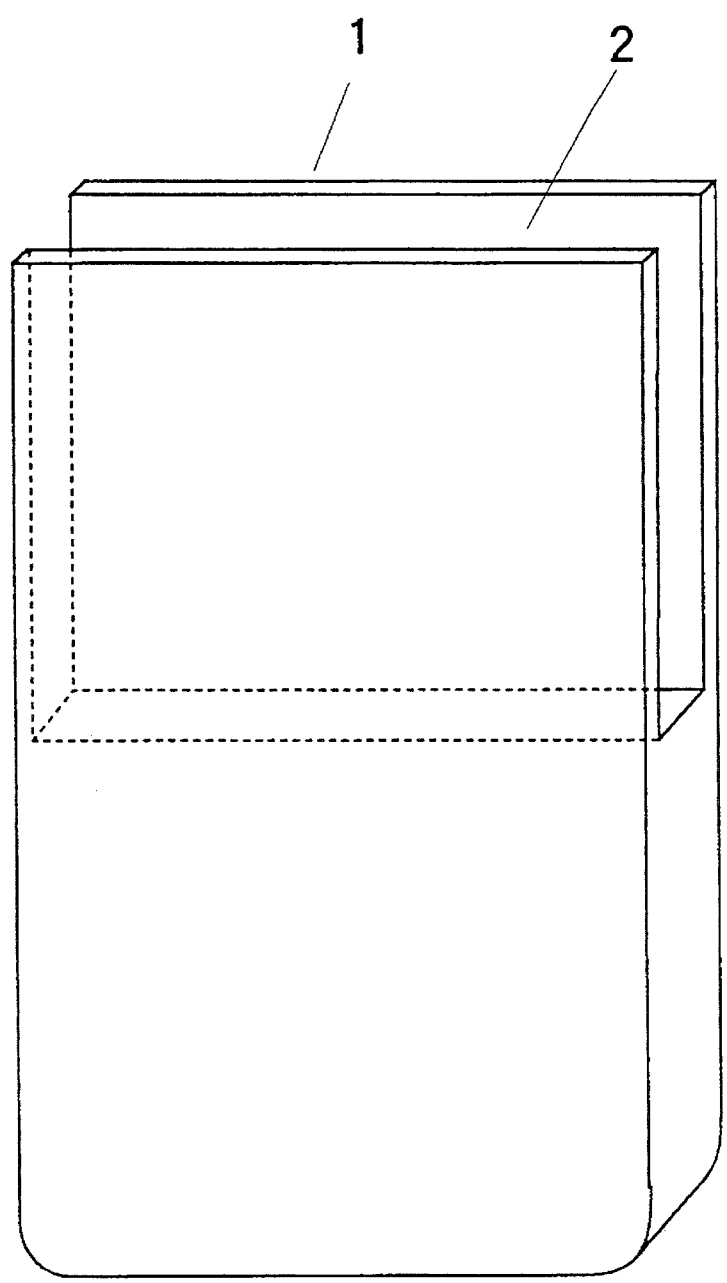
FIG. 4 is a diagrammatic perspective view of still another form of the filter device holder (sandwiching type) to be used in the method of the present invention.

Filter device holder 1 of FIG. 4 is a sandwiching type holder having a couple of opposite walls which provide recess 2 therebetween. Like the enclosing type holder of FIGS. 3(*a*) and 3(*b*), a sandwiching type holder of FIG. 4 is advantageous in that accommodation of the filter device into and removal of the filter device from the recess of the filter device holder can be readily performed.

Figure 5:
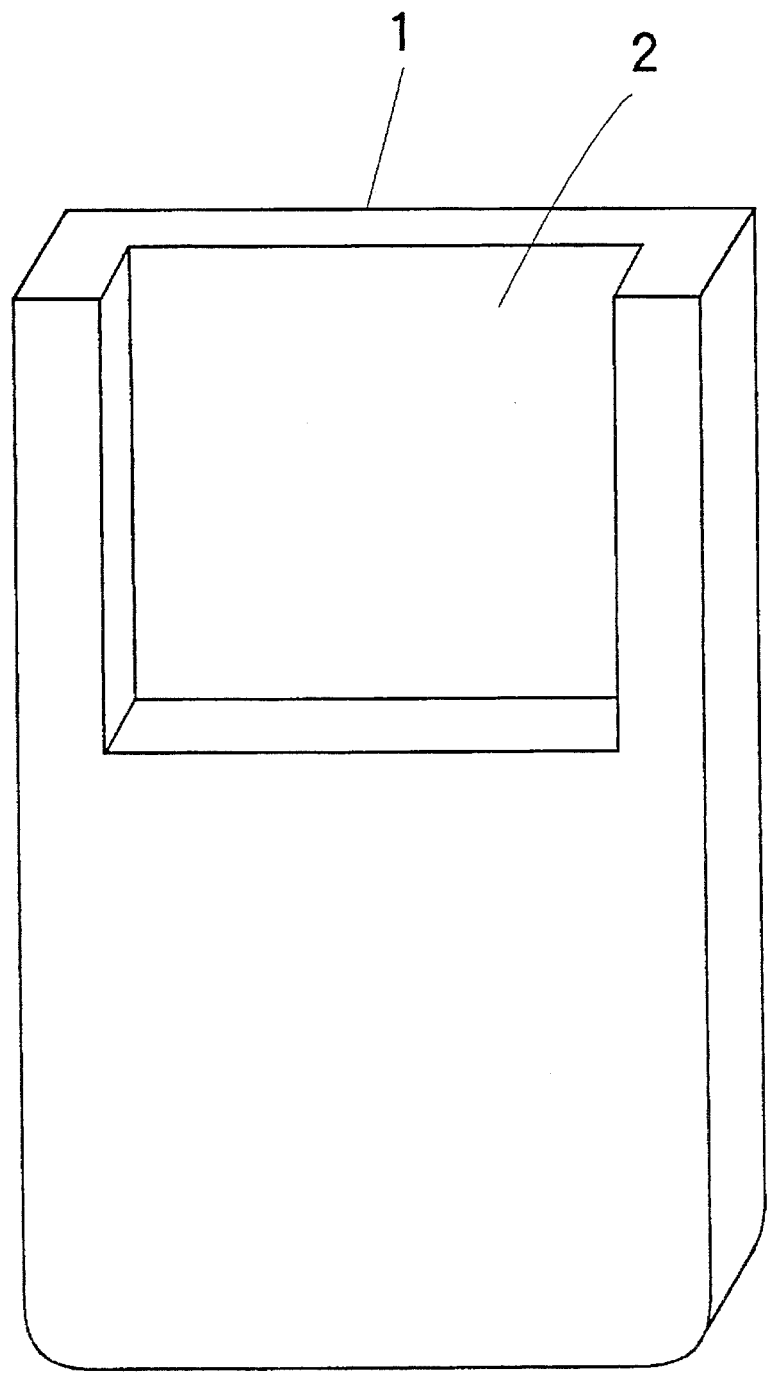
FIG. 5 is a diagrammatic perspective view of a further form of the filter device holder (seat type) to be used in the method of the present invention.

Filter device holder 1 of FIG. 5 is a seat type holder which has recess 2 having a configuration which can fit well with the contour of the filter device, with only one flat surface portion of the filter device being exposed. The seat type holder of FIG. 5 is advantageous in that when the filter device has a projection, such as inlet and outlet nozzles, and/or an angular portion, the projection and/or angular portions can be effectively covered by the seat-like recess.

Figure 6:
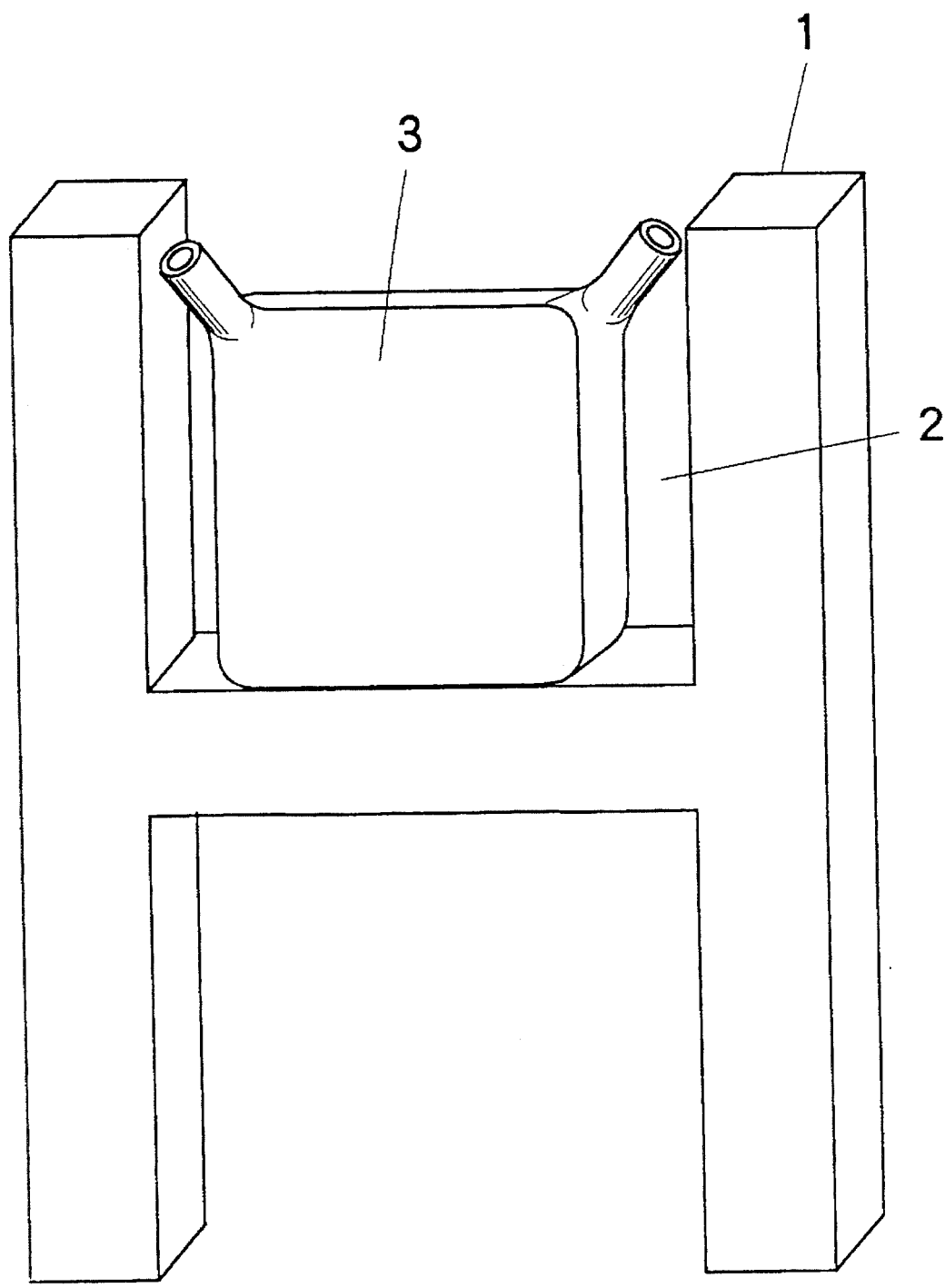
FIG. 6 is a diagrammatic perspective view of still a further form of the filter device holder (H type) to be used in the method of the present invention, shown with a filter device held thereby.

Filter device holder 1 of FIG. 6 is an H type holder which has recess 2 which receives filter device 3 only along the periphery thereof. The H type holder of FIG. 6 is advantageously constructed to have the same thickness as that of the filter device, so that the filter device holder need not any additional thickness for providing a space for receiving the filter device. Therefore, the H type holder of FIG. 6 is advantageous when the thickness of the filter device holder having the filter device held thereby is desired to be as small as possible, for example when the volume of the centrifuge cup is relatively small or the total volume of the blood bags is relatively large.

The method of the present invention can also be suitably practiced even when the centrifugation is performed using a centrifuge inner cup placed inside the centrifuge cup. A centrifuge inner cup, which is made of a plastic material is conventionally used for facilitating the accommodation of a multiple blood bag system into a centrifuge cup. When a multiple blood bag system is to be accommodated in a centrifuge cup without using an inner cup, it is necessary to take out the centrifuge cup (which is made of metal and is heavy in weight) from the centrifuge system every centrifugation operation for accommodating the multiple blood bag system therein. When a plastic, centrifuge inner cup, which is light in weight and can be easily handled, is employed, the multiple blood bag system is first placed in the plastic inner cup and the inner cup having the multiple blood bag system placed therein can be readily accommodated in the centrifuge cup, without taking out the centrifuge cup from the centrifuge every centrifugation operation. When the method of the present invention is practiced using a centrifuge inner cup, the multiple blood bag system is placed in a centrifuge inner cup having an inner bottom floor, and the inner cup having the multiple blood bag system placed therein is entirely accommodated in the centrifuge cup, so that the multiple blood bag system is indirectly accommodated in the centrifuge cup through the centrifuge inner cup.

The centrifuge inner cup may be of a type having a single chamber or of a type having a plurality of chambers which are designed to separate the filter device and blood bags from one another or separate the filter device from the blood bags. With respect to the centrifuge inner cup having a plurality of chambers, the centrifuge inner cup may be a cup made of a plurality of smaller cups connected to one another or a cup partitioned into a plurality of chambers.

In the method of the present invention, the filter device of a multiple blood bag system comprising a flat casing can be accommodated readily, fittedly and stably into the centrifuge cup together with the blood bags in a compact fashion without the need for using any additional securing means, such as an adhesive tape, so that the accommodation of a multiple blood bag system into the centrifuge cup can be readily performed without any additional cumbersome operations. Further, in the method of the present invention, not only extends the filter device holder in a direction perpendicular to the inner bottom floor of the centrifuge cup, but also the filter device is received by the recess of the filter device holder in a manner such that a flat surface of the flat casing of the filter device is perpendicular to the inner bottom floor of the centrifuge cup, so that the danger of damage to the filter device and the blood bags is extremely reduced.

PREFERRED EMBODIMENT OF THE INVENTION

The present invention will now be described in detail with reference to the following Example and Comparative Example, which should not be construed as limiting the scope of the present invention.

EXAMPLE

Filter device holder 1 shown in FIG. 2 is provided, which has the following dimensional characteristics: a height (indicated by character a in FIG. 2) of 12.5 cm, a width (indicated by character b in FIG. 2) of 8 cm, a thickness (indicated by character c in FIG. 2) of 7 mm and a wall thickness (indicated by character d in FIG. 2) of the pocket as recess 2 of 2 mm.

The filter device holder is one which has been prepared by the following method. A rectangular sheet of a butadiene rubber having a height of 5 cm, a width of 7 cm and a thickness of 3 mm (rubber sheet A), and a rectangular sheet of a butadiene rubber having a height of 12.5 cm, a width of 17 cm and a thickness of 2 mm (rubber sheet B) are prepared. The rubber sheet A is set up so that a side thereof having a length of 7 cm (width) becomes a bottom. The rubber sheet B is surrounded around the set-up rubber sheet A, so that the rubber sheet A is entirely enclosed by the lower portion of the rubber sheet B. The rubber sheet B is bonded at its both ends by means of an adhesive and, at the same time, the inner surface of the lower portion of the rubber sheet B is also bonded to the entire peripheral surface of the set-up rubber sheet A by means of the same adhesive, to thereby obtain a filter device holder having a pocket as recess 2 as shown in FIG. 2.

A non-woven fabric of polyethylene terephthalate is packed in a flat casing made of polycarbonate, to thereby prepare leukocyte-removing filter device 3, wherein the casing has blood inlet 7 and blood outlet 8 at the upper corners thereof as shown in FIG. 9(a). Using the thus prepared leukocyte-removing filter device, a multiple blood bag system as described in U.S. Pat. No. 4,596,657 is prepared which is comprised of a primary bag and two satellite bags, one of which is connected to the primary bag through the leukocyte-removing filter device. A mixture (500 ml) of 437 ml of bovine whole blood and 63 ml of CPD solution is charged into the primary bag (blood collection bag).

A centrifugation is conducted as follows. Filter device 3 is disposed in the pocket (recess 2) of filter device holder 1 so that both inlet 7 and outlet 8 of filter device 3 are directed upward as shown in FIG. 2. Then, as shown in FIG. 1, filter device holder 1 holding filter device 3 is accommodated in iron centrifuge cup 4 (having an inner diameter of 10 cm and a depth of 15 cm) together with blood bags 5, 6 and 6' so that filter device holder 1 holding filter device 3 received by recess 2 is disposed between primary bag 5 and satellite bag 6 (this multiple blood bag system does not have bag 6" shown in FIG. 1). Then, the multiple blood bag system accommodated in the centrifuge cup is subjected to centrifugation at a centrifugal force of 5000 G for 10 minutes, using a centrifuge (CR783, manufactured and sold by Hitachi Koki Co., Ltd., Japan), thereby separating the blood into an upper layer and a lower layer.

Thereafter, the leukocyte-removing operation is conducted as follows. The upper layer composed of plasma in primary bag 5 is transferred into satellite bag 6' (which is not connected to filter device 3 but connected to primary bag 5). Then, primary bag 5 is lifted to and hung at a height of 1.5 m, and the lower layer composed of a red cell concentrate in primary bag 5 is allowed to flow through filter device 3 by gravity. The leukocyte-removed red cell concentrate from filter device 3 is collected in satellite bag 6.

The same procedure as described above (i.e., the production of a multiple blood bag system and an experiment using the same) is repeated 24 times. As a result, it is found that, in each time, filter device 3 received by recess 2 of filter device holder 1 can be readily, fittedly and stably accommodated into centrifuge cup 4 together with blood bags 5, 6 and 6', and the centrifugation can be conducted without causing any damage to filter device 3 and blood bags 5, 6 and 6'.

Comparative Example

Substantially the same procedure as in Example is repeated except that the centrifugation is performed without using filter device holder 3. That is, filter device 3 as such is disposed between primary bag 5 and satellite bag 6 without the use of a filter device holder.

As a result, in many experiments, the filter device falls out of the original position at the upper portion of the centrifuge cup down to the inner bottom floor of the centrifuge cup during the centrifugation, or the inlet or the outlet of the filter device is pressed against the inner side wall of the centrifuge cup during the centrifugation. Further, in two experiments, a damage to the filter device is observed after the centrifugation.

What is claimed is:

1. A method for separating a blood material into leukocyte-removed blood component products, which comprises:

(1) providing a multiple blood bag system comprising a primary bag containing a blood material, a leukocyte-removing filter device fluid-tightly connected to an outlet of said primary bag through a tube and at least one satellite bag fluid-tightly connected to an outlet of said filter device through a tube, said filter device comprising a flat case having a blood inlet and a blood outlet, and a filter material disposed in said case and communicated on one side thereof to said blood inlet and on the other side thereof to said blood outlet, and (2) in either order, (a) centrifuging the blood material or a leukocyte-removed blood product obtained in step (b) from the blood material, using a centrifuge cup having said multiple blood bag system accommodated therein, to separate said blood material or leukocyte-removed blood product into blood components, and (b) filtering leukocytes from the blood material or a blood component separated in step (a) from the blood material, using said filter device of the multiple blood bag system to obtain a leukocyte-removed blood product, wherein in step (a), the centrifugation is performed with said filter device of the multiple blood bag system being held by a filter device holder having one side with a substantially flat dimension which is disposed in said centrifuge cup in a manner such that a plane of the filter device holder which extends along said side with said substantially flat dimension is perpendicular to an inner bottom floor of the centrifuge cup and the filter device holder is retained between blood bags of said multiple blood bag system or between a blood bag of said multiple blood bag system and an inner side wall of said centrifuge cup, said filter device holder having a recess substantially conforming to the shape of the flat case of said filter device and disposed in a direction opposite to said inner bottom floor of the centrifuge cup, said filter device being received by the recess of said filter device holder in a manner such that a flat surface of the flat case of the filter device is perpendicular to said inner bottom floor of the centrifuge cup.

2. The method according to claim 1, wherein said recess is located in an upper portion of said filter device holder.

3. The method according to claim 1, wherein said filter device has on the flat case a projection and/or an angular portion and said filter device holder has a portion thereof covering said projection and/or angular portion.

4. The method according to claim 1, wherein said filter device holder is made of an elastic material at least at a portion of said holder which contacts said filter device.

5. The method according to claim 1, wherein said multiple blood bag system is placed in a centrifuge inner cup having an inner bottom floor, and said inner cup having said multiple blood bag system placed therein is entirely accommodated in said centrifuge cup, so that said multiple blood bag system is indirectly accommodated in said centrifuge cup through said centrifuge inner cup.

* * * * *